Figure 1:
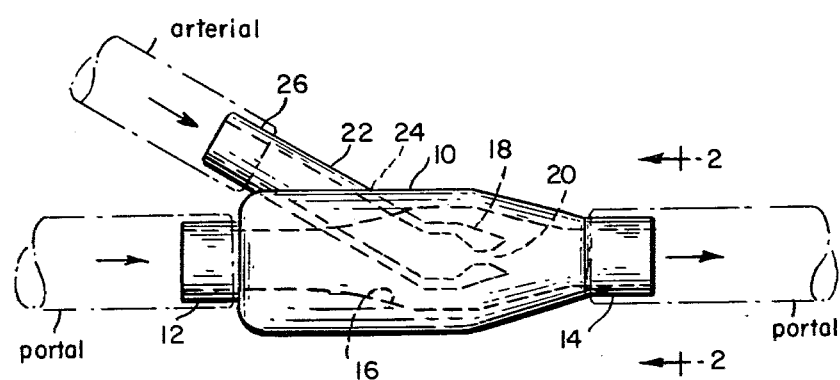

United States Patent [19]

Olson

[11] 4,335,711
[45] * Jun. 22, 1982

[54] METHOD AND DEVICE FOR SUPPLYING VENOUS PRESSURE IN A PORTAL VEIN

[76] Inventor: Edward A. Olson, 107 Plymouth Mobile Estates, Plymouth, Mass. 02360

[*] Notice: The portion of the term of this patent subsequent to May 27, 1997, has been disclaimed.

[21] Appl. No.: 92,539

[22] Filed: Nov. 8, 1979

Related U.S. Application Data

[62] Division of Ser. No. 924,615, Jul. 14, 1978, Pat. No. 4,104,525.

[51] Int. Cl.³ ............................................. A61B 19/00
[52] U.S. Cl. .................................................. 128/1 R
[58] Field of Search ................... 128/335, 214 R, 348, 128/350, 1 R

[56] References Cited

U.S. PATENT DOCUMENTS

| | | | |
|---|---|---|---|
| 3,877,461 | 4/1975 | Bucalo | 128/1 R |
| 3,946,734 | 3/1976 | Dedrick et al. | 128/1 R |
| 3,990,434 | 11/1976 | Free | 128/1 R |
| 3,991,743 | 11/1976 | Bucalo | |
| 4,204,525 | 5/1980 | Olson | 128/214 |

Primary Examiner—Stephen C. Pellegrino
Attorney, Agent, or Firm—Robert T. Gammons

[57] ABSTRACT

A method and device for pressurizing the flow of venous blood in the portal vein to a diseased liver. The method comprises introducing arterial blood into the flow path of the venous blood in the portal vein. The device comprises an elongate chamber, the ends of which are adapted to be connected to the ends of the portal vein from which a section has been removed to provide a substitute flow path for the removed section, interiorly thereof a nozzle facing in the direction of flow and a conductor, one end of which is connected to the nozzle and the other end of which is connected to an arterial vein.

4 Claims, 2 Drawing Figures

METHOD AND DEVICE FOR SUPPLYING VENOUS PRESSURE IN A PORTAL VEIN

This is a division of application Ser. No. 924,615 filed July 14, 1978 U.S. Pat. No. 4,104,525.

BACKGROUND OF INVENTION

A diseased or damaged liver, for whatever reason, builds up a back pressure which prevents normal flow of the venous blood through the portal vein to the liver so that deterioration of the liver is aggravated in proportion to the dearth of blood supplied to it. Normally, a liver tends to rebuild itself if supplied with a sufficient amount of venous blood and, in the past, it has been suggested to supplement the flow of venous blood to the liver by mechanical devices, for example, a pump to force flow of venous blood to the liver at a pressure to overcome the resistance of the liver to receipt of the venous blood at normal pressure. No practical way of accomplishing this has been devised since such treatment, to be effective, must be continuous and any treatment involving a pump would necessarily have to be administered by qualified persons under controlled conditions at periodic intervals such as in a hospital. It is the purpose of this invention to provide a method and device for continuously supplementing the flow pressure of venous blood to the liver which may be contained entirely internally of the patient so as to require no participation on his part or supplementary assistance.

SUMMARY OF INVENTION

As herein illustrated, the method comprises supplying venous blood to the liver at a pressure in excess of the back pressure tending to prevent delivery thereof by the portal vein thereto comprising introducing arterial blood to the flow path of the venous blood in the portal vein adjacent to the liver. The method includes interposing a connector into the portal vein so as to define a flow chamber in line with the flow path of the venous blood and injecting arterial blood from an adjacent arterial vein into said chamber at the center line of flow of the venous blood thereto and in the direction of flow of the venous blood. In a broader sense, the method comprises supplementing the flow pressure in a vein in the direction of flow comprising connecting a vein in which there is a higher flow pressure in the vein requiring supplemental flow pressure so as to introduce blood from the vein containing the higher pressure flow into the stream of blood of the lower pressure flow in the direction of flow.

The device comprises an elongate chamber and a tubular part entering the chamber defining a nozzle concentric with the chamber, said part within the chamber being provided with a discharge orifice facing in the direction of one end of the chamber. The chamber has end portions designed to be received into the ends of the portal vein from which a section has been removed and tied to provide a substitute flow path for the removed section and the exterior end of the tubular portion is designed to be connected to an arterial vein to conduct arterial blood into the flow path of the venous blood in the portal vein. The chamber is comprised of a plastic material compatible with the blood and the flow passage therethrough increases in cross sectional area from one end to approximately its mid length and then decreases from its mid length to the opposite end. The discharge orifice is situated substantially mid length of the chamber and defines a restricted opening.

Figure 2:
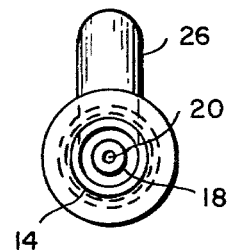

The invention will now be described with reference to the accompanying drawings, wherein:

FIG. 1 is an elevation of the device for introducing arterial blood from an arterial vein to the portal vein to increase the flow of venous blood to the liver; and FIG. 2 is an elevation taken in the direction of the line 2—2 of FIG. 1.

The method as related comprises essentially introducing blood from an artery containing a higher flow pressure to a vein of lower flow pressure requiring supplemental pressure in the direction of flow of the stream of blood in the vein of lower pressure to increase the flow in the direction of flow. More specifically, the method comprises supplying venous blood to the liver at a pressure in excess of the back pressure tending to prevent delivery thereof by the portal vein to the liver comprising introducing arterial blood to the flow path of the venous blood in the portal vein adjacent the liver.

This is achieved by means of the device shown in FIGS. 1 and 2 which is adapted to be placed in the body of a patient troubled with a diseased liver condition. The device comprises an elongate chamber 10 having at its ends portions 12 and 14 which are adapted to be received into the ends of the portal vein from which a section has been removed and tied therein to provide a substitute flow path for the removed section. The chamber 10, as illustrated, contains an elongated flow passage or path 16 which increases in cross section from the end 12 to substantially mid length and then decreases from mid length to the end 14. Within the enlarged portion of the chamber which is substantially midway between its ends, there is mounted a nozzle 18 provided with a restricted orifice 20 which is situated forwardly of the enlarged portion where the passage commences to decrease. The nozzle faces in the direction of flow through the chamber, that is, in a direction to supplement the flow of blood through the portal vein to the liver. A conductor 22 is connected at one end to the nozzle through an opening 24 in the side of the chamber and the opposite end 26 of the conductor 22 is adapted to be connected to an arterial vein.

The flow pressure in a portal vein is in the order of 10 to 20 millimeters and the pressure in an arterial vein is in the order of 120 to 140 millimeters. Thus, it is evident that the pressure developed by the arterial blood flowing into the chamber 10 into the path of flow of the venous blood will entrain and increase the total pressure within the chamber in the direction of the flow path and such pressure is sufficient to overcome the resistance the liver offers to receiving venous blood at the relatively low pressure of 10 to 20 millimeters. This can be achieved without detriment to the liver and provides the advantage that it continuously supplies a sufficient quantity of venous blood to the liver to assist it in regenerating itself.

The device is comprised of any suitable material which is not deleterious to the blood nor objectionable to the normal body functions, is relatively compact so that it can be introduced without discomfort, and is sufficiently durable so that it will function for an indefinite period of time. Materials which are suitable are plastics and stainless steel.

It should be understood that the present disclosure is for the purpose of illustration only and includes all modifications or improvements which fall within the scope of the appended claims.

I claim:

1. A device for increasing the flow of venous blood to the liver comprising an elongate chamber and a tubular part entering the chamber defining an orifice concentric with the chamber and facing in the direction of one end of the chamber, said chamber having end portions designed to be received into the ends of the portal vein from which a section has been removed and tied to provide a substitute flow path for the removed section and the exterior end of the tubular portion being designed to be connected to an arterial vein to conduct arterial blood into the flow path of the venous blood in the portal vein, said chamber and tube being comprised of suitable material compatible with the blood.

2. A device for increasing the flow of venous blood to the liver comprising an elongate chamber and a tubular part entering the chamber defining an orifice concentric with the chamber and facing in the direction of one end of the chamber, said chamber having end portions designed to be received into the ends of the portal vein from which a section has been removed and tied to provide a substitute flow path for the removed section and the exterior end of the tubular portion being designed to be connected to an arterial vein to conduct arterial blood into the flow path of the venous blood in the portal vein, wherein the chamber has a flow passage which increases in cross-sectional area from one end to approximately its mid-length and then decreases its mid-length to the opposite end and wherein the orifice is situated forwardly of the mid-length of the chamber.

3. A device for increasing the flow of venous blood to the liver comprising an elongate chamber and a tubular part entering the chamber defining an orifice concentric with the chamber and facing in the direction of one end of the chamber, said chamber having end portions designed to be received into the ends of the portal vein from which a section has been removed and tied to provide a substitute flow path for the removed section and the exterior end of the tubular portion being designed to be connected to an arterial vein to conduct arterial blood into the flow path of the venous blood in the portal vein and wherein the orifice defines a restricted opening.

4. A device for increasing the flow of venous blood to the liver comprising an elongate chamber and a tubular part entering the chamber defining an orifice concentric with the chamber and facing in the direction of one end of the chamber, said chamber having end portions designed to be received into the ends of the portal vein from which a section has been removed and tied to provide a substitute flow path for the removed section and the exterior end of the tubular portion being designed to be connected to an arterial vein to conduct arterial blood into the flow path of the venous blood in the portal vein, wherein the chamber has at each end a portion of reduced section for insertion into a vein end.

* * * * *